United States Patent [19]
Lehr

[11] Patent Number: 5,434,329
[45] Date of Patent: Jul. 18, 1995

[54] TREATMENT OF SPENT REFINERY CAUSTIC

[75] Inventor: James S. Lehr, Wilmington, Del.

[73] Assignee: Star Enterprise, Houston, Tex.

[21] Appl. No.: 83,147

[22] Filed: Jun. 25, 1993

[51] Int. Cl.$^6$ .......................... C07C 7/00; C07C 7/10; C01B 17/16
[52] U.S. Cl. .................... 585/803; 585/836; 585/854; 423/224; 423/233; 423/234; 423/243.11; 423/243.08
[58] Field of Search ................ 585/803, 836, 854; 423/224, 233, 234, 243.11, 243.08

[56] References Cited

U.S. PATENT DOCUMENTS

| | | | |
|---|---|---|---|
| 1,918,153 | 7/1933 | Wagner . | |
| 1,942,054 | 1/1934 | Garrison | 196/32 |
| 1,945,002 | 2/1934 | Shoeld et al. | 23/150 |
| 3,591,332 | 7/1971 | George et al. | 23/64 |
| 3,841,961 | 10/1974 | Shiha et al. | 162/29 |
| 3,932,587 | 1/1976 | Grantham et al. | 423/422.563 |
| 4,041,129 | 8/1977 | Foster et al. | 423/234 |
| 4,562,300 | 12/1985 | La Foy | 585/854 |

OTHER PUBLICATIONS

Chen, Yi Shon, et al.—"Spent Caustic Treatment and Disposal"—1988—Prod. Ind. Waste Conf., vol. Date 1987, 42nd., 429-36.
Hills, M. R.—"Electrolytic Treatment of Effluents'-'—1969—Effluent Water Treatment J., 9(12), 647-50, 652-4; 1970, 10(1), 33, 35-6.
Berne, F., et al.—"A Way to Treat Phenolic Caustic'-'—Hydrocarbon Process, vol. 66, Issue 10, p. 52.
Willenbrink, R.—"Wastewater Reuse and In-Plant Treatment"—1973—Water—73—Amer. Ins. of Chemical Engs. Symposium Series, vol. 70, No. 136, pp. 671-674.
Asylova, K. T., et al.—"Disposal of Sour Caustics with Utilization of Carbonated Products"—1984—Chem. Technol. Fuel Oils, vol. 19, No. 5-6, pp. 218-221—Khim. Tekhnol. Topliv Masel, vol. 19, No. 5, pp. 12-13.
Starkey, J.—"Off-Site Disposal Eliminated with Wet Air Oxidation"—Chemical Processing Nov., 1982.

*Primary Examiner*—Anthony McFarlane
*Assistant Examiner*—Nhat D. Phan
*Attorney, Agent, or Firm*—John R. Casperson

[57] ABSTRACT

A hydrocarbon stream is washed with caustic solution to reactively remove hydrogen sulfide and produce a spent caustic solution containing sulfide reaction products. The spent caustic solution is stripped with concentrated carbon dioxide to reactively remove the sulfides and produce an overhead hydrogen sulfide stream and a bicarbonate-containing bottoms stream. The hydrogen sulfide stream can be converted to elemental sulfur in a Claus unit or to sulfuric acid in a sulfuric acid plant. The bicarbonate solution can be washed with liquid hydrocarbon to remove mercaptans and phenols in further preparation for disposal.

15 Claims, 1 Drawing Sheet

TREATMENT OF SPENT REFINERY CAUSTIC

BACKGROUND OF THE INVENTION

In one aspect, this invention relates to the treatment of spent refinery or petrochemical plant caustic. In another aspect, this invention relates to a process for sulfur removal and recovery from refinery and petrochemical plant streams. In yet another aspect, this invention pertains to apparatus for carrying out the treatment of refinery and petrochemical plant streams.

Petroleum refineries and petrochemical plants use catalytic cracking and thermal cracking processes such as fluid or delayed coking to convert heavy hydrocarbons into lighter cuts. Cuts ranging in boiling point from fuel gas to kerosene are produced. These are often treated with aqueous solutions of sodium hydroxide or potassium hydroxide to remove acidic components such as hydrogen sulfide, mercaptans and phenols. Other refinery operations such as crude oil distillation produce cuts that are often treated in a similar way. The caustic scrubbing liquor retains these compounds as sodium or potassium salts such as sodium sulfide, sodium mercaptide, etc. A purge stream of spent caustic scrubbing liquor is discharged. This spent caustic scrubbing liquor is classified as D003 (Reactive Sulfide) Resource Conservation and Recovery Act (RCRA) hazardous waste. As such, these spent caustic liquors must be treated to a standard of "deactivation to remove the characteristic of reactivity."

A process for deactivating the spent caustic for proper and safe disposal would be very desirable.

OBJECTS OF THE INVENTION

It is an object of this invention to provide a process for extracting acidic components from refinery and petrochemical plant streams.

It is another object of this invention to provide a process for removing sulfides from a spent caustic stream.

It is a further object of this invention to provide a process for extracting mercaptans and phenols from a spent caustic stream.

Another object of this invention is to remove or extract odorous compounds from a spent caustic stream.

Another object of this invention is to accomplish the forgoing objects in a manner which retains the alkalinity value of the spent caustic stream.

Another object of this invention is to accomplish the forgoing objects in a manner to recover the sulfur in a useful form.

It is yet another object of this invention to provide an apparatus for carrying out the above processes.

SUMMARY OF THE INVENTION

In one embodiment of the invention, a spent caustic aqueous stream is introduced into an upper end of a stripping tower. An enriched carbon dioxide-containing gas stream is introduced into the lower end of said stripping tower. The spent caustic aqueous stream is countercurrently contacted with the carbon dioxide gas stream to form an aqueous bicarbonate solution and liberate hydrogen sulfide gas. A stripper overhead gas stream containing the hydrogen sulfide gas is withdrawn from the upper end of the stripping tower. A stripper bottoms stream containing the aqueous bicarbonate solution is withdrawn from the lower end of the stripping tower. The invention removes sulfides from the spent caustic so that the spent caustic can be more easily disposed of. The sulfides are handled in such a way to lead to their recovery in a sulfur or sulfuric acid unit. Mercaptans can be easily extracted from the stripper bottoms with hydrocarbon.

In accordance with certain embodiments of the invention, there is provided an apparatus which is well suited for carrying out the above process. The apparatus comprises a stripping tower. A conduit means connects the caustic wash unit with an upper portion of the stripping tower. The apparatus preferably further comprises a settler vessel. A conduit means connects a lower portion of the stripping tower with the settler vessel. The apparatus preferably further comprises a sulfur recovery unit. A conduit means connects an upper portion of the stripping tower with the sulfur recovery unit.

BRIEF DESCRIPTION OF THE DRAWING

The drawing schematically illustrates certain features of one embodiment of the present invention.

DETAILED DESCRIPTION OF THE PREFERRED EMBODIMENTS

Figure 1:
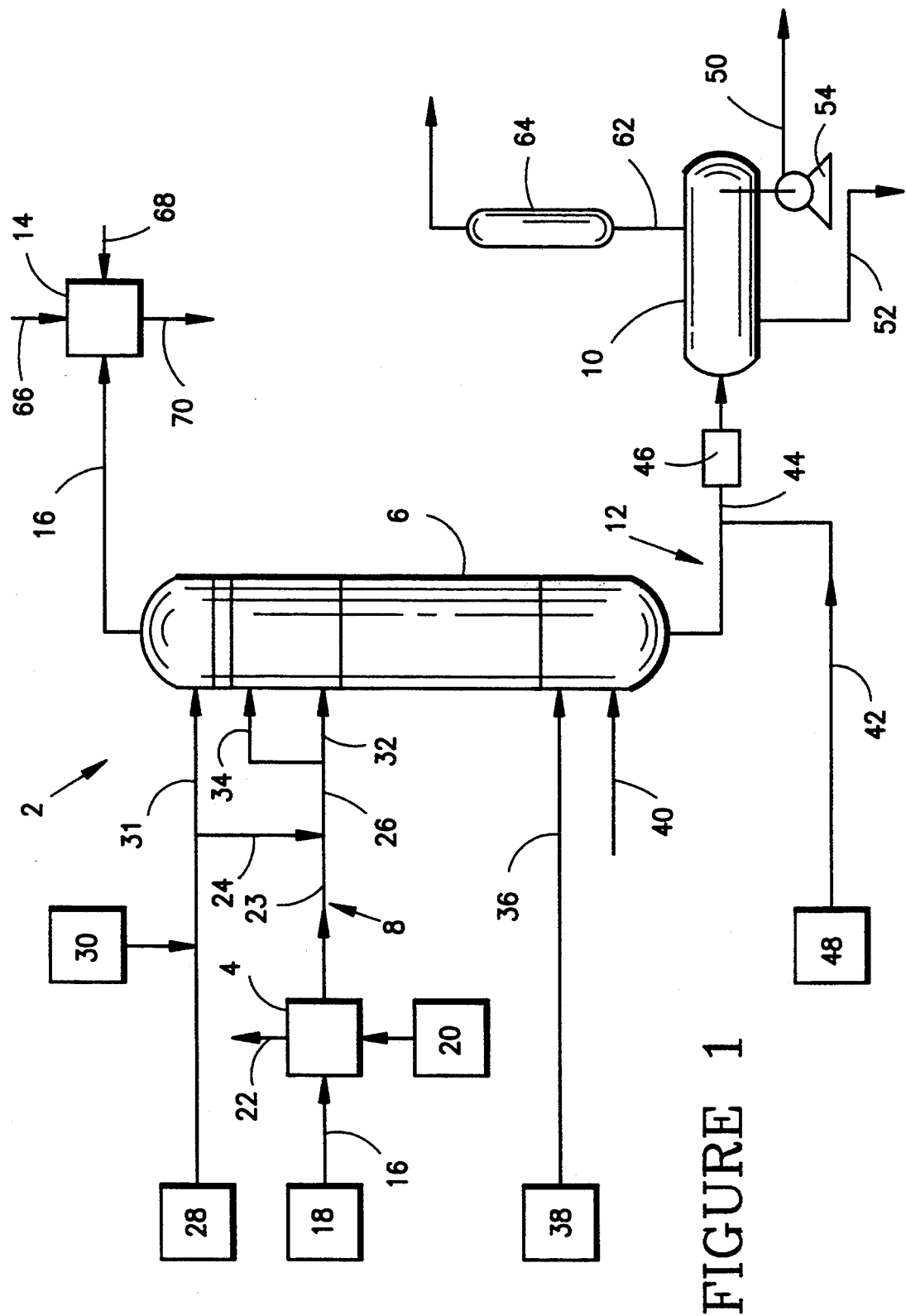

In accordance with certain embodiments of the invention, there is provided an apparatus 2 for treating spent refinery caustic which can be recovered from a caustic wash unit 4. The apparatus 2 comprises a stripping tower 6. A conduit means 8 connects the caustic wash unit 4 with an upper portion of the stripping tower 6. The apparatus 2 preferably further comprises a settler vessel 10. A conduit means 12 connects a lower portion of the stripping tower 6 with the settler vessel 10. The apparatus 2 preferably further comprises a sulfur recovery unit 14. A conduit means 16 connects an upper portion of the stripping tower 6 with the sulfur recovery unit 14.

In the caustic wash unit 4, a liquid hydrocarbon stream carried by the conduit means 16 from a hydrocarbon source 18 is treated. Suitable streams to be treated in accordance with the invention include propane, butane and naphtha, for example. The hydrocarbon stream contains acid components including hydrogen sulfide gas. The hydrocarbon stream is treated with an aqueous sodium or potassium hydroxide solution from a source 20 to separate such acid components from said hydrocarbon stream. This procedure produces a caustic-treated hydrocarbon stream 22 which is essentially free of acid components and a caustic aqueous stream 23 carried by the means 8.

The strength of the starting caustic solution can vary over a wide range, but using a concentrated solution will result in a longer run time between turnaround and produces a lower volume of spent caustic solution which must be disposed of. For example, the use of a starting solution containing in the range of about 3% to about 30% by weight of fresh caustic is expected to provide good results. Good results have been obtained using a starting solution containing in the range of about 10 percent to about 25 percent of fresh caustic, especially about a 20% caustic solution, which provides a good balance between freeze point and caustic strength. It is desirable to discharge the spent caustic and replenish with fresh caustic prior to hydrogen sulfide breakthrough.

Where a concentrated caustic solution is used in the wash step, it is preferred that the stream 23 be diluted prior to introduction into the tower 6. Preferably, a sufficient amount of an aqueous diluent stream 24 is mixed with the spent caustic aqueous stream 23 to form a diluted caustic stream 26. The stream 26 preferably has a sufficiently low caustic content and/or a sufficiently high temperature to substantially prevent carbonates and bicarbonates from crystallizing in the stripping tower. Due to temperatures in the stripping tower, it is preferred that the temperature of the stream 26 be at least about 130 degrees F. (54 degrees C.) but beneath the boiling point. Temperature can be easily controlled by regulating the flow of hot water from a source 28 and cold water from a source 30 each in flow communication with conduit means 8. Generally speaking, the aqueous stream entering the stripping tower contains in the range of about 0.1 to about 10 percent by weight of caustic, usually in the range of about 0.7 to about 7 percent, and preferably in the range of about 3 to about 5 percent. For example, where a 20 weight percent caustic solution is employed in the caustic wash step, it can be diluted 4 to 1 with water to reduce solidification problems.

In one embodiment of the invention, the spent caustic aqueous stream 26 is divided into a first portion 32 and a second portion 34. The first portion 32 is introduced into the stripping tower 6 at a first location and the second portion 34 is introduced into the stripping tower at a second location between the first location and the upper end of the stripping tower. Generally speaking, between about 3% and about 30% of the stream 26 will be routed into the tower 6 as the second portion 34. Usually, between about 5% and about 25% of the stream 26 will be introduced into the tower as the second portion 34.

In the stripping tower 6, the spent caustic aqueous stream 26 enters an upper portion of the tower 6 preferably near the upper end. The stream contains reaction products between hydrogen sulfide and aqueous caustic solution. An enriched carbon dioxide-containing gas stream 36 is introduced into a lower portion of the stripping tower 6, preferably near the lower end. The carbon dioxide-containing gas stream 36 flows upwardly through the tower countercurrently contacting the spent caustic aqueous stream flowing downwardly through the tower. Preferably, the tower contains tray means such as trays and or packing to facilitate obtaining equilibrium conditions for the fluids being withdrawn from the tower. A chemical reaction occurs which forms an aqueous bicarbonate solution and liberates hydrogen sulfide gas. The hydrogen sulfide gas is withdrawn from the tower 6 as the stripper overhead gas stream 16 from an upper end of the stripping tower. The aqueous bicarbonate solution is withdrawn from the tower 6 as a stripper bottoms stream via conduit means 12.

Generally speaking, in the range of about 1 mole to about 3 moles of carbon dioxide gas are introduced into the stripping tower for each mole of alkalinity which enters the tower in the spent caustic stream. Alkalinity can also be expressed in terms of base equivalents, as determined by titration to neutrality with acid equivalents. The base species in the spent alkaline solution will generally be sodium or potassium hydroxides and sulfides and the sodium or potassium salts of mercaptans and the sodium and potassium salts of phenolic compounds such as phenols and cresylic acids. Usually, in the range of about 1.6 to about 2.6 moles of carbon dioxide are introduced into the stripping tower for each mole of alkalinity which is introduced into the stripping tower in the spent caustic aqueous stream. Most preferably, about 2 moles of carbon dioxide is introduced into the stripping tower for each mole of entering alkalinity because an amount near this ratio was used in a test unit at a stripping temperature of about 130 degrees F. and found to be a sufficient amount to remove more than 98% of the hydrogen sulfide and mercaptan sulfur as well as more than 98% of the phenolic compounds.

It is desirable to employ an enriched carbon dioxide stream 36 so that the flow and carbon dioxide content of the overhead stream 16 will be low. The carbon dioxide stream 36 is taken from a source 38. The source 38 generally contains about 30 to about 100 mole % carbon dioxide, usually about 60 to about 100 mole % carbon dioxide and preferably about 80 to about 100 mole % carbon dioxide. Substantially pure carbon dioxide can be used with good results.

Generally speaking, it is important to maintain the temperature of the tower in the range of about 100 degrees F. to about 200 degrees F. (38–93 degrees C.). In a preferred embodiment of the invention, a steam stream 40 is introduced into the lower portion of the stripping tower in an amount sufficient to maintain the stripping tower temperature in the range of about 110 to about 190 degrees F. (43–88 degrees C.), preferably in the range of 120 to about 180 degrees F. (49–82 degrees C.), and most preferably in the range of 130 to 170 degrees F. (54–77 degrees C.). Operations in the most preferable range have provided good results.

In a preferred embodiment of the invention, a water wash is introduced into the upper portion of the stripping tower via conduit means 31. The conduit means 31 preferably empties into the tower 6 near the upper end. The water wash is introduced into the tower 6 in an amount sufficient to substantially prevent the carryover of salts in the stripper overhead gas stream. Preferably, water having a temperature of at least 130 degrees F. is used for the water wash. The temperature of the water wash can be easily regulated by mixing hot and cold water from the sources 28 and 30 to form the water wash stream.

The stripper bottoms stream 12 is mixed with a liquid hydrocarbon stream 42 to form a settler vessel feed stream 44 containing a two phase liquid mixture. The relative amounts of the streams 12 and 42 can be varied over a wide range—for example in the range of 0.1:1 to 10:1, such as in the range of 0.3:1 to 3:1. Suitable liquid hydrocarbon streams include C5+ hydrocarbons having an initial boiling point in the range of about 95 to about 630 degrees F. (35–330 degrees C.). For example, the stream 42 can be withdrawn from a source 48 of liquid hydrocarbon which contains naphtha, gasoline or gas oil. Preferably, the settler vessel feed stream 44 is passed through a mixing device 46 such as an inline mixer or a pump to form a two-phase liquid mixture which is then introduced into the settler vessel 10. The two phase liquid mixture is separated in the settler vessel into an upper hydrocarbon phase and a lower aqueous phase. The upper hydrocarbon phase is withdrawn as stream via conduit means 50 from an upper portion of the settler vessel. It generally contains mercaptans and phenols which have been extracted from the aqueous phase. If required, a pump 54 can be positioned in the conduit means 50 to convey the hydrocarbon phase to further processing, such as to fractionation. The lower aqueous phase is generally withdrawn as a stream via a conduit means 52 from a lower portion of the settler vessel. It is routed for proper and safe disposal, although it may be stored for a while in tankage.

Under certain conditions, a gas phase may form in the settler 10. In such event, it may be withdrawn via from the settler 10 via a line 62 connected to an upper portion of the settler, passed through an activated absorbent bed such as carbon canister 64, and vented or flared.

The stripper overhead gas stream 16 flows to the sulfur recovery unit 14. The stripper overhead gas stream generally contains water vapor, hydrogen sulfide, mercaptans, carbon dioxide and phenols. The stripper overhead gas stream generally contains at least about 95% of the theoretical hydrogen sulfide which enters the stripping tower, based on the hydrogen sulfide reaction products in the spent caustic stream. Suitable sulfur recovery units are any of those which can accommodate a gas stream having the above characteristics. Claus units, which produce liquid sulfur, and sulfuric acid plants or regenerators are suitable. In the most preferable set up, the overhead gas stream is combusted with an oxidant gas stream 66 in a first stage of the unit and is then reacted with additional hydrogen sulfide stream 68 in a second stage of the unit. Sulfur in a nonvolatile form is recovered as a stream 70 from the unit.

The invention is further illustrated by the following example.

EXAMPLE

A spent caustic stream from an oil refinery was diluted 4:1 with water and fed to the top of a column containing two sections of packing. The column was formed from schedule 40 pipe and measured 52¼ inches by ¾ inches O.D. The upper section of packing was 25 inches in length and the lower section of packing was 23 inches in length. The packing measured 0.16×0.16 inches, and was Protruded Distillation Packing from Scientific Development Co., Box 795, State College, Pa. Carbon dioxide was fed to the bottom of the column in the ratio of 2.1 moles CO2 per mole of alkalinity, where "alkalinity" is based on a titration of the spent caustic with HCl from its initial pH to a pH of 8.5. The temperature was controlled at 130° F. CO2 flow was 8 liters/hr @ 60 degrees F., 1 atm. The spent caustic (1.198 sp.gr.) flow rate was 48.5 gm/hr. It was diluted with a water flow of 156.9 gm/hr. Samples were analyzed as follows:

|  | Spent Caustic | Bottoms |
| --- | --- | --- |
| H2S, wt % as S | 1.17 | 0.013 |
| Mercaptans, wt % as S | 3.83 | 0.057 |
| Phenols, mol/lit | 0.72 | 0.01 |
| OH—, mol/lit | 1.11 | 0 |
| pH |  | 8.5 |
| Na, wt % | 8.3 |  |
| K, wt % | 0.6 |  |

The bottoms stream was contacted with naphtha in a separatory funnel and shaken for approximately two minutes. This was done at the following ratios:

3 parts naphtha: 1 part stripper bottoms 1 part naphtha: 1 part stripper bottoms 1 part naphtha: 3 parts stripper bottoms In each case the aqueous phase was analyzed and found to contain <0.003 wt % mercaptans and <0.005 mol/lit phenols.

While certain preferred embodiments of the invention have been hereinabove described, the invention is not to be construed as so limited, except to the extent such limitations are found in the claims.

I claim:

1. A process comprising
washing a hydrocarbon stream which contains acid components including hydrogen sulfide gas with an aqueous caustic solution selected from the group consisting of sodium hydroxide solution and potassium hydroxide, solution to separate such acid components from said hydrocarbon stream thereby forming a caustic treated hydrocarbon stream and a spent caustic stream containing reactions products formed by a reaction between the hydrogen sulfide and the aqueous caustic solution;
mixing an aqueous diluent stream with said spent caustic stream to form a diluted spent caustic stream;
introducing the diluted spent caustic aqueous stream into an upper portion of a stripping tower wherein a sufficient amount of the diluent stream is mixed with the spent caustic stream to substantially prevent carbonates and bicarbonates from crystallizing in the stripping tower;
introducing an enriched carbon dioxide-containing gas stream into a lower portion of said stripping tower;
countercurrently contacting said spent caustic aqueous stream with said carbon dioxide-containing gas stream at a stripping temperature in the range of about 100 degrees F. to about 200 degrees F. to form an aqueous bicarbonate solution and liberate hydrogen sulfide gas;
withdrawing a stripper overhead gas stream containing the hydrogen sulfide gas from the upper end of the stripping tower; and
withdrawing a stripper bottoms stream containing the aqueous bicarbonate solution from the lower end of the stripping tower.

2. A process as in claim 1 further comprising
mixing said stripper bottoms stream with a liquid hydrocarbon stream to form a settler vessel feed stream containing a two phase liquid mixture;
introducing said settler vessel feed stream into a settler vessel; and phase separating said two phase liquid mixture into an upper hydrocarbon phase and a lower aqueous phase in said settler vessel.

3. A process comprising;
a) introducing a spent caustic aqueous stream into an upper portion of a stripping tower, said spent caustic stream containing reaction products formed by a reaction between hydrogen sulfide and concentrated aqueous caustic solution, said concentrated aqueous caustic solution having a starting caustic content in the range of about 10 percent to about 25 percent based on weight, wherein said spent caustic aqueous stream is divided into a first portion and a second portion, and the first portion is introduced into the stripping tower at a first location and the second portion is introduced into the stripping tower at a second location between the first location and the upper end of the stripping tower;
b) introducing an enriched carbon dioxide-containing gas stream into a lower portion of said stripping tower, wherein in the range of about 1.0 to about 3.0 moles of carbon dioxide are introduced into the stripping tower for each mole of alkalinity which is introduced into the stripping tower in the spent caustic aqueous stream;

c) countercurrently contacting said spent caustic aqueous stream with said carbon dioxide—containing gas stream at a stripping temperature in the range of about 100 degrees F. to about 200 degrees F. to form an aqueous bicarbonate solution and liberate hydrogen sulfide gas;

d) withdrawing a stripper overhead gas stream containing the hydrogen sulfide gas from the upper end of the stripping tower; and e) withdrawing a stripper bottoms stream containing the aqueous bicarbonate solution from the lower end of the stripping tower.

4. A process as in claim 3 further comprising introducing a steam stream into the lower end of the stripping tower in an amount sufficient to maintain the stripping tower temperature in the range of about 110 to about 190 degrees F.

5. A process as in claim 1 further comprising introducing a water wash into the upper end of the stripping tower in an amount sufficient to substantially prevent the carryover of salts in the stripper overhead gas stream.

6. A process as in claim 2 further comprising
mixing the liquid hydrocarbon stream with the stripper bottoms stream upstream of an in-line mixing device;
withdrawing the upper hydrocarbon phase from an upper portion of the settler vessel;
withdrawing the lower aqueous phase from a lower portion of the settler vessel.

7. A process as in claim 1 wherein in the range of about 1.6 to about 2.6 moles of carbon dioxide are introduced into the stripping tower for each mole of alkalinity which is introduced into the stripping tower in the spent caustic aqueous stream and the carbon dioxide content of the enriched carbon-dioxide containing gas stream is in the range of about 30 mole % to about 100 mole %.

8. A process as in claim 7 further comprising maintaining the stripping tower temperature is in the range of about 120 to about 180 degrees F.

9. A process as in claim 4 further comprising
introducing the steam stream into the lower portion of the stripping tower so that the stripping tower temperature is maintained in the range of about 130 to about 170 degrees F.;
maintaining the temperature of the water wash above about 130 degrees F.; and controlling the amount of carbon dioxide introduced into the stripping tower so that in the range of about 1.9 to about 2.3 moles of carbon dioxide are introduced into the stripping tower for each mole of alkalinity which is introduced into the stripping tower in the spent caustic aqueous stream.

10. A process as in claim 7 wherein the upper hydrocarbon phase contains phenols and mercaptans and the enriched carbon dioxide-containing stream contains in the range of about 60 mole % to about 100 mole % of carbon dioxide.

11. A process as in claim 3 wherein the stripper overhead gas stream contains at least about 95% of the theoretical hydrogen sulfide which enters the stripping tower, based on the hydrogen sulfide reaction products in the spent caustic stream wherein in the range of about 3% to about 30% of the spent caustic aqueous stream is introduced into the stripping tower at the second location.

12. A process as in claim 1 wherein the caustic treated hydrocarbon stream is selected from the group consisting of a propane stream, a butane stream, and a naphtha stream.

13. A process as in claim 2 wherein the upper hydrocarbon phase comprises a C5+ hydrocarbon having an initial boiling point in the range of about 95 degrees to about 630 degrees F. and said upper hydrocarbon phase contains mercaptans and phenols.

14. A process as in claim 13 wherein the upper hydrocarbon phase is selected from the group consisting of naphtha, gasoline and gas oil and the enriched carbon dioxide-containing stream contains in the range of about 90 mole % to about 100 mole % of carbon dioxide.

15. A process as in claim 6 further comprising flowing the spent caustic aqueous stream over a set of trays in the stripping tower and collecting the lower aqueous phase which has been withdrawn from the settler vessel.

* * * * *